(12) United States Patent
Sartor et al.

(10) Patent No.: US 8,414,578 B2
(45) Date of Patent: Apr. 9, 2013

(54) SELF CONTAINED, GAS-ENHANCED SURGICAL INSTRUMENT

(75) Inventors: Joe D. Sartor, Longmont, CO (US); Michael Hogan, Boulder, CO (US); Gene H. Arts, Berthoud, CO (US); Ronald J. Podhajsky, Boulder, CO (US); Arlan J. Reschke, Longmont, CO (US)

(73) Assignee: Covidien AG (CH)

( * ) Notice: Subject to any disclaimer, the term of this patent is extended or adjusted under 35 U.S.C. 154(b) by 5 days.

(21) Appl. No.: 12/622,248

(22) Filed: Nov. 19, 2009

(65) Prior Publication Data

US 2010/0069902 A1     Mar. 18, 2010

Related U.S. Application Data

(63) Continuation of application No. 11/048,577, filed on Feb. 1, 2005, now Pat. No. 7,628,787.

(60) Provisional application No. 60/541,326, filed on Feb. 3, 2004.

(51) Int. Cl.
*A61B 18/14* (2006.01)

(52) U.S. Cl.
USPC .......................................................... 606/41

(58) Field of Classification Search ............... 606/32–50
See application file for complete search history.

(56) References Cited

U.S. PATENT DOCUMENTS

| | | |
|---|---|---|
| 2,708,933 A | 5/1955 | August |
| 2,828,747 A | 4/1958 | August |
| 3,434,476 A | 3/1969 | Shaw et al. |
| 3,569,661 A | 3/1971 | Ebeling |
| 3,692,973 A | 9/1972 | Oku et al. |
| 3,699,967 A | 10/1972 | Anderson |
| 3,832,513 A | 8/1974 | Klasson |
| 3,834,433 A * | 9/1974 | Thompson ..................... 141/392 |
| 3,838,242 A | 9/1974 | Goucher |
| 3,903,891 A | 9/1975 | Brayshaw |

(Continued)

FOREIGN PATENT DOCUMENTS

| | | |
|---|---|---|
| DE | 3710489 | 11/1987 |
| DE | 4139029 | 6/1993 |

(Continued)

OTHER PUBLICATIONS

Hernandez et al., "A Controlled Study of the Argon Beam Coagultor for Partial Nephrectomy", The Journal of Urology, vol. 143, May (J. Urol. 143: pp. 1062-1065, 1990).

(Continued)

*Primary Examiner* — Michael Peffley
*Assistant Examiner* — Ronald Hupczey, Jr.

(57) ABSTRACT

An electrosurgical apparatus for coagulating tissue includes an elongated housing and an electrode located adjacent the distal end of the housing. The electrode can be connected to a source of electrosurgical energy. At least one actuator is included which electrosurgically energizes the electrode. The apparatus also includes a relatively small gas cylinder which contains a pressurized gas consisting of inert gas and which is selectively seated in the housing. Upon actuation of the actuator, gas is dispersed under pressure from the gas cylinder to the electrode and is ionized prior to the distribution of the gas into the operating field.

20 Claims, 2 Drawing Sheets

U.S. PATENT DOCUMENTS

| | | |
|---|---|---|
| 3,970,088 A | 7/1976 | Morrison |
| 3,987,795 A | 10/1976 | Morrison |
| 3,991,764 A | 11/1976 | Incropera et al. |
| 4,014,343 A | 3/1977 | Esty |
| 4,019,925 A | 4/1977 | Nenno et al. |
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |
| 4,060,088 A | 11/1977 | Morrison, Jr. et al. |
| 4,209,018 A | 6/1980 | Meinke et al. |
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A * | 3/1992 | Fleenor ............... 606/42 |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmonesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Brown et al. |
| 5,306,238 A | 4/1994 | Fleenor |
| 5,324,283 A | 6/1994 | Heckele |
| 5,330,469 A * | 7/1994 | Fleenor ............... 606/40 |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,423,741 A | 6/1995 | Frank |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,700,260 A | 12/1997 | Cho et al. |
| 5,716,365 A | 2/1998 | Goicoechea et al. |
| 5,720,745 A | 2/1998 | Farin et al. |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,139,519 A | 10/2000 | Blythe |
| 6,141,985 A | 11/2000 | Cluzeau et al. |
| 6,149,648 A | 11/2000 | Cosmescu |
| 6,197,026 B1 | 3/2001 | Farin et al. |
| 6,206,878 B1 * | 3/2001 | Bishop et al. ............... 606/49 |
| 6,213,999 B1 | 4/2001 | Platt |
| 6,264,650 B1 | 7/2001 | Hovda et al. |
| 6,299,592 B1 | 10/2001 | Zander |
| 6,348,051 B1 | 2/2002 | Farin et al. |
| 6,458,125 B1 | 10/2002 | Cosmescu |
| 6,475,217 B1 | 11/2002 | Platt |
| 6,558,383 B2 | 5/2003 | Cunningham et al. |
| 6,616,660 B1 | 9/2003 | Platt |
| 6,666,865 B2 | 12/2003 | Platt |
| 6,852,112 B2 | 2/2005 | Platt |
| 2001/0018587 A1 | 8/2001 | Yamamoto |
| 2002/0022838 A1 | 2/2002 | Cunningham et al. |
| 2003/0093073 A1 | 5/2003 | Platt |
| 2003/0144654 A1 | 7/2003 | Hilal |
| 2004/0088029 A1 | 5/2004 | Yamamoto |
| 2005/0015086 A1 | 1/2005 | Platt |
| 2005/0070894 A1 | 3/2005 | McClurken |
| 2006/0052771 A1 | 3/2006 | Sartor et al. |
| 2006/0200122 A1 | 9/2006 | Sartor et al. |

FOREIGN PATENT DOCUMENTS

| | | |
|---|---|---|
| DE | 4326037 | 2/1995 |
| DE | 9117019 | 4/1995 |
| DE | 195 37 897 | 3/1997 |
| DE | 9117299 | 4/2000 |
| DE | 19848784 | 5/2000 |
| DE | 29724247 | 8/2000 |
| EP | 0 447 121 A2 | 9/1991 |
| EP | 0 612 535 | 8/1994 |
| EP | 956827 | 11/1999 |
| EP | 1 090 599 | 4/2001 |
| EP | 1 127 551 A1 | 8/2001 |
| EP | 1 561 430 A1 | 8/2005 |
| EP | 1 570 798 A2 | 9/2005 |
| EP | 1570798 | 9/2005 |
| EP | 1 595 507 A2 | 11/2005 |
| FR | 1340509 | 9/1963 |
| GB | L014995 | 12/1965 |
| JP | 61-159953 | 10/1986 |
| SU | 1438745 | 11/1988 |
| WO | WO 9100709 | 1/1991 |
| WO | WO 91/13593 | 9/1991 |
| WO | WO 93/03678 | 3/1993 |
| WO | WO 96/24301 | 8/1996 |
| WO | WO 96/27337 | 9/1996 |
| WO | WO 01/62333 | 8/2001 |
| WO | WO 02/058762 | 8/2002 |
| WO | WO 2005/016142 | 2/2005 |

OTHER PUBLICATIONS

Ward et al., "A Significant New Contribution to Radical Head and Neck Surgery", Arch Otolaryngology, Head and Neck Surg., vol. 115 pp. 921-923 (Aug. 1989).

International Search Report EP09171599.5 dated Mar. I6, 2010.

International Search Report EP09171600 dated Dec. 10, 2009.

International Search Report EP10180912 dated Dec. 8, 2010.

Silverstein et al., "Thermal Coagulation Therapy for Upper Gatrointestinal Bleeding", Advanced Therapeutic Endoscopy, pp. 70-84 (1990).

Waye et al., "Techniques in Therapeutic Endoscopy", W.B. Saunders Company, Philadelphia, PA., pp. 1.7-1.15 (1987).

Grund et al., "Endoscopic Argon Plasma . . . Flexible Endoscopy" Surgery and Allied Technologies, No. 1, vol. 2, pp. 42-46 (Feb. 1994).

Farin et al., "Technology of Argon Plasma . . . Endoscopic Applications" Endoscopic Surgery and Allied Technologies, No. 1, vol. 2, pp. 71-77 (Feb. 1994).

Brand et al., "Electrosurgical Debulking of Ovarian Cancer: A New Technique Using the Argon Beam Coagulator", Gynecologic Oncology 39 pp. 115-118 (1990).

Hemandez et al., "A Controlled Study of the Argon Beam Coagultor for Partial Nephrectomy". The Journal of Urology, vol. 143, May (J. Urol. 143: pp. 1062-1065, 1990).

Ward et al.. "A Significant New Contribution to Radical Head and Neck Surgery". Arch Otolaryngology, Head and Neck Surg., vol. 115 pp. 921-923 (Aug. 1989).

Mark H. Mellow, "The Role of Endoscopic Laser Therapy in Gastrointestinal Neoplasms", Advanced Therapeutic Endoscopy, pp. 17-21 (1990).

Silverstein et al., "Thermal Coagulation Therapy for Upper Gatrointestinal Bleeding", Advanced Therapeutic Endoscopy, pp. 79-84 (1990).

Way et al., "Techniques in Therapeutic Endoscopy", W.B. Saunders Company, Philadelphia, PA., pp. 1.7-1.15 (1987).

* cited by examiner

SELF CONTAINED, GAS-ENHANCED SURGICAL INSTRUMENT

CROSS REFERENCE TO RELATED APPLICATION

This application is a continuation of U.S. application Ser. No. 11/048,577 entitled "Self Contained, Gas-Enhanced Surgical Instrument" filed on Feb. 1, 2005, now U.S. Pat. No. 7,628,787, by Joe Don Sartor, et al., which claims the benefit of and priority to U.S. Provisional application Ser. No. 60/541,326 entitled "Self Contained, Gas-Enhanced Surgical Instrument" filed on Feb. 3, 2004, the entire contents of these applications being incorporated by reference herein.

BACKGROUND

The present disclosure relates to devices for use in open, laparascopic or endoscopic procedures for treating tissue. More particularly, the present disclosure relates to gas-enhanced surgical instruments, including electrosurgical instruments for treating tissue, which include a self-contained and/or selectively replaceable gas supply for use during medical, e.g., surgical applications.

BACKGROUND OF RELATED ART

Devices, hereafter understood to include instruments, for treating tissue, for example, for tissue division, dissection, ablation, or for arresting blood loss and coagulating tissue are well known. For example, several prior art instruments employ thermic coagulation (heated probes) to arrest bleeding. However, since the probe must come into close contact with the bleeding tissue, the probe may adhere to the tissue during probe removal and may possibly cause repeat bleeding. Many surgical probes also produce an undesirable buildup of eschar on or proximate the probe tip which detrimentally affects the efficiency of the surgical instrument. Other instruments direct high frequency electric current through the tissue to stop bleeding. Again, eschar adherence may occur with these instruments. In addition, with both types of instruments, the depth of the coagulation is difficult to control.

One or more prior art devices have attempted to resolve certain of the above-noted and other problems by providing a tube-like coagulation instrument in which an ionizable gas, for example argon gas, is forced from a remote gas supply through the instrument and ionized by an electrode prior to the gas being emitted from the distal end of the instrument towards the bleeding tissue. Other instruments have been developed which include an electrode for ionizing a stream of remotely provided ionizable gas which exits the distal end of the instrument at a rate of less than about 1 liter/minute. Providing the gas at this flow rate is believed to effectively cloud the tissue area and create an ionizable gas "atmosphere" to gently coagulate the tissue. The atmosphere of ionized gas is beneficial, for example, because it helps focus an arc of energy adjacent the electrode, and it displaces oxygen from the area and reduces oxidative stress of the tissue.

It is thought that electrosurgical instruments which utilize ionizable gas to effectively coagulate tissue all utilize a gas hose (or other hose-like connection) to connect the instrument to a remote, removable large supply of gas for use during the operation. Typically, the gas supply or source is situated in close proximity to the operating room where the gas is stored in large containers for repeated use during the operation and subsequent operations. As can be appreciated, having a gas supply hose attached to the electrosurgical instrument can be distracting to surgeons, burdensome (especially during intense and complicated surgical procedures, e.g., those utilizing multiple instruments simultaneously) and prone to causing entanglements or interference with the other electrosurgical cords attached to the instrument(s). Thus, a need exists to develop a self-contained gas-enhanced electrosurgical instrument and small cylinders of pressurized gas utilizable therewith which eliminate the need for gas hoses and remotely located and large gas storage containers. Electrosurgical instruments according to this disclosure that include a self-contained, replaceable, small gas cylinder of pressurized inert gas, preferably argon gas, or mixture of inert gases, and the small cylinders of inert gas according to the disclosure, provide advantages over the use of prior large, remote containers of ionizable gas for various generic uses, including for dispersing debris or fluid at surgical sites. The instruments and small containers are easy to handle and manipulate. They can include one or more of a variety of features, e.g., flow and/or pressure regulators, pressure relief valves, gauges, indicators, sensors and control systems that can be tailored to fit the surgical procedure, that can be controlled at hand and in sight by the user, and that accordingly provide the opportunity for obtaining optimized results. The small containers and their contents can also be tailored, e.g., in terms of use of a particular inert gas or gas mixture, gas pressure, volume, flow rate, etc. to fit the particular instrument and/or procedure, thereby also providing the opportunity for obtaining optimized results.

SUMMARY

An electrosurgical instrument for providing ionized inert gas to a surgical site comprises a frame having a proximal end and a distal end, the distal end having a port for emitting gas, a receptacle for seating a cylinder of pressurized gas therein, a cylinder seated in the receptacle and containing pressurized gas consisting of inert gas, an active electrode located adjacent the distal end of the frame, the electrode being connected to a source of electrosurgical energy, a channel for channeling the pressurized gas to the electrode, and at least one actuator for actuating the flow of pressurized inert gas from the cylinder to the active electrode, and for actuating the delivery of electrosurgical energy from the source to the active electrode for ionizing the inert gas for use at the surgical site.

In an embodiment, the at least one actuator for actuating the flow of pressurized gas can also operate as an actuator for actuating the delivery of the electrosurgical energy.

In an embodiment, the at least one actuator can be adapted to actuate the release of pressurized gas from the cylinder prior to actuating the delivery of the electrosurgical energy.

In an embodiment, there is a first actuator for actuating the flow of pressurized gas from the cylinder and a second actuator for actuating delivery of the electrosurgical energy from the source to the active electrode.

There can be one or more elements for activating the first actuator prior to actuating the second actuator. The at least one actuator for actuating the flow of pressurized gas can comprise a valve. The cylinder can include a sealed outlet and the valve can include a coupling for engaging and breaking the seal of the cylinder. The valve can include a plenum positioned between the coupling and the channel for regulating flow of pressurized gas to the channel, and a flow regulator for regulating the flow of pressurized gas to the electrode. The valve can comprise a pressure regulator for regulating the pressure of the gas. There can be included in the instrument a pressure regulator for regulating the pressure of the gas that flows to the active electrode. There can be included in the instrument a first flow regulator for selectively regulating the flow of pressurized gas from the cylinder, and, optionally, a second flow regulator for selectively regulating the flow of pressurized gas to the electrode to below a selected level.

In an embodiment, the at least one actuator for actuating the flow of pressurized inert gas from the cylinder, and for actuating the delivery of electrosurgical energy, is selectively adjustable to selectively adjust the flow of pressurized gas and the delivery of electrosurgical energy. The first actuator can be adapted to selectively adjust the flow of pressurized gas from the cylinder, and/or the second actuator can be adapted to selectively adjust the amount of electrosurgical energy that is delivered to the active electrode. A pressure regulator can include a pressure relief valve in communication with the cylinder for relieving the pressure of the pressurized gas in the cylinder. There can be included in the instrument a pressure relief valve for relieving the pressure of the pressurized gas, and there can be included a flow limiter for limiting the flow of pressurized gas to the electrode.

In an embodiment, the electrosurgical instrument can include a valve for controlling the flow of pressurized gas from the cylinder, at least one actuator for actuating the flow of pressurized inert gas from the cylinder to the active electrode, and for actuating the delivery of electrosurgical energy from the source to the active electrode, the at least one actuator being movable from a first position to at least a subsequent position, such movement operatively causing at least one electrical output signal to be transmitted to the flow control valve and to the source, the at least one output signal being correlated to the degree of movement of the at least one actuator, and the flow control valve and the source of electrosurgical energy being respectively adapted to deliver a corresponding flow of pressurized gas and a corresponding amount of electrosurgical energy to the active electrode. The electrosurgical instrument can include at least one transducer electrically connected between the at least one actuator and the flow control valve and between the at least one actuator and the source, to provide the at least one electrical output signal to be transmitted to the flow control valve and to the source.

In an embodiment, the electrosurgical instrument includes a valve for controlling the flow of pressurized gas from the cylinder, wherein the first actuator and the second actuator are each selectively adjustable by movement from a first position to at least a second position, such application of movement operatively transmitting a respective output signal to the flow control valve and to the source that is correlated to the amount of applied movement of the respective first and second actuators, the flow control valve and the source of electrosurgical energy each correspondingly supplying an amount of gas and electrosurgical energy to the active electrode. At least one transducer can be electrically connected between the first actuator and the flow control valve and between the second actuator and the source to transmit the respective output signals to the respective flow control valve and source.

In embodiments, the electrosurgical instrument can include a flow regulator and a sensor in electrical communication with the flow regulator, the sensor being for sensing a selected condition adjacent the distal end of the frame and automatically controlling the regulation of flow of pressurized gas to the active electrode. The instrument can include a sensor in electrical communication with a pressure relief valve, for sensing a selected condition at the surgical site and automatically activating the pressure relief valve to relieve the pressure of the pressurized gas in the cylinder. The instrument can include a sensor in electrical communication with the second actuator for actuating delivery of electrosurgical energy from the source, the sensor being for sensing a selected condition at the surgical site and automatically modulating or terminating the delivery of energy to the active electrode.

In embodiments, the electrosurgical instrument can include a pressure regulator to reduce the pressure of the gas from its pressure level in the cylinder to one or more selected lower levels.

In embodiments, the electrosurgical instrument is configured to produce inert gas enhanced electrosurgical fulguration, for example, to coagulate, or produce a cutting or sealing effect in body tissue. The electrosurgical instrument can be configured and adapted for use in open, endoscopic and or laparoscopic applications.

The electrosurgical instrument can include a sensor for sensing a condition, the sensor being electrically connected to a safety pressure relief valve for venting pressure from the cylinder before it is removed from the receptacle.

In embodiments, the active electrode can be located proximally of the port of the frame. The instrument can include a member that extends distally from the distal end of the frame, and the active electrode can be supported on the member in a position distal of the port.

The cylinder, as used with, seated in or part of the electrosurgical instrument, or separately as a cylinder suitable for use, for example, in an electrosurgical instrument for medical applications, contains pressurized gas consisting of inert gas, preferably argon gas, or a mixture of inert gases. The cylinder has a volume of about 100 cc or less. The pressure of the as-filled gas in the cylinder can be about 3000 psi or less. The cylinder preferably provides a flow rate of from about 0.2 liters/min. to about 4 liters/min., and/or a nominal flow rate of about 2 liters/min. It can be visibly coded, for example with color, to indicate a characteristic of the cylinder or of the pressurized gas, e.g., that it contains a particular inert gas or mixture of inert gases, or the flow rate of the pressurized inert gas, or the as-filled flow rate of the contained pressurized inert gas or that the cylinder is suitable for use in a particular electrosurgical instrument or procedure.

In an embodiment, the cylinder contains pressurized gas and is suitable for use in an electrosurgical instrument for medical applications. The cylinder comprises a body containing a pressurized gas consisting of inert gas, the body having a proximal end, a distal end and a seal sealing an outlet, wherein the volume of the cylinder is about 100 cc's or less. The cylinder can include: a safety pressure stop valve operative upon or after rupture of the seal to automatically prevent flow of the gas from the outlet when the cylinder is removed from the instrument; a safety pressure release valve to safely control release of cylinder internal gas overpressure; a gauge to continually measure and indicate to a user the volume of pressurized gas in the cylinder; a refill valve to allow refilling of the cylinder with inert pressurized gas without removing the cylinder from a hand-held instrument; and/or a flow control valve for selectively controlling gas flow from the cylinder through the outlet. The cylinder can include an indicator for indicating to the user that a characteristic of the pressurized gas in the cylinder is below a selected level.

DETAILED DESCRIPTION

Figure 1:
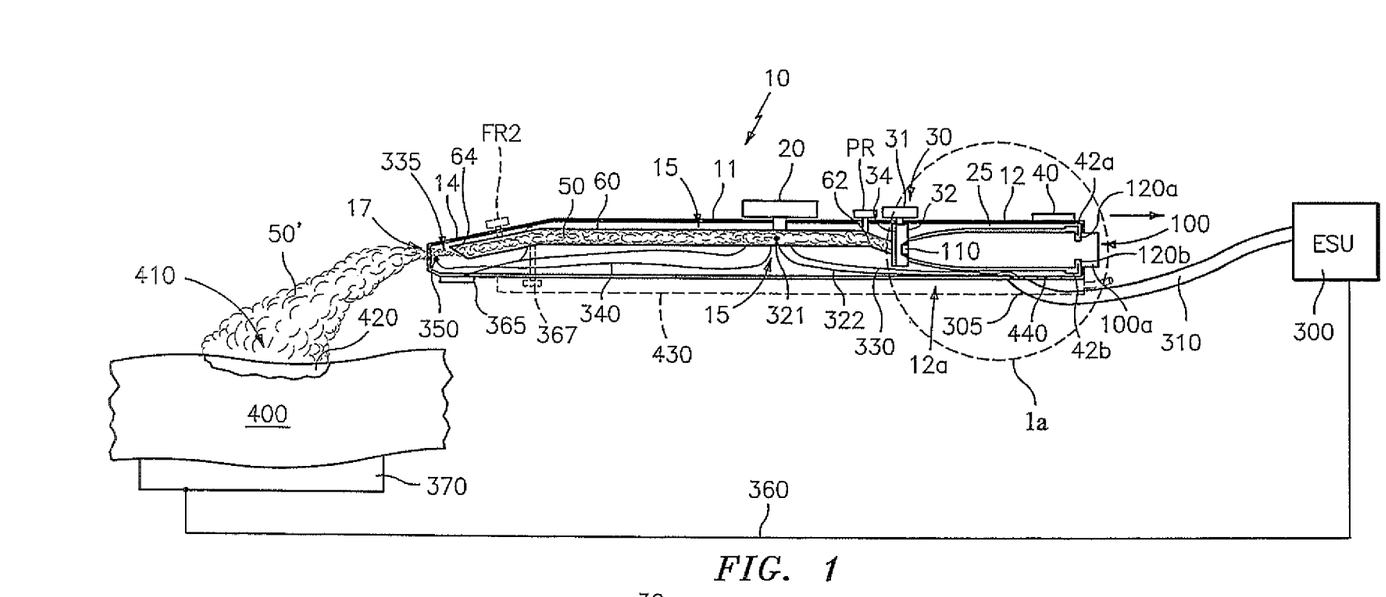
FIG. 1 is a side schematic vertical sectional view of an electrosurgical coagulator according to the present disclosure.

This application discloses embodiments of electrosurgical apparatus or instruments that are adapted for use with, and preferably include a self-contained supply of pressurized inert gas for providing ionizable gas to a surgical or operative site. FIG. 1 shows an embodiment of a gas-enhanced electrosurgical instrument, here, a gas coagulator, generally designated 10, for coagulating tissue. Preferably and as shown, coagulator 10 is dimensioned to be pencil-like or hand-held, including robotically, for use during open surgical procedures, however, it is envisioned that a similar instrument or coagulator may be configured, for example, with a pistol grip or handle and seals to prevent loss of gas, and dimensioned for laparoscopic or endoscopic surgical procedures. Although, the basic operating features of an open electrosurgical coagulator 10 are described herein, the same or similar operating features may be employed on or used in connection with a laparoscopic or endoscopic electrosurgical coagulator or instrument, manually or robotically operated, without departing from the scope of the present disclosure. The term "electrosurgical energy" herein refers to any type of electrical energy which may be utilized for medical procedures.

As shown in FIG. 1, coagulator 10 includes a frame, shown as an elongated housing 11, having a proximal end 12, a distal end 14 and an elongated cavity 15 extending therethrough, for supporting and/or housing a plurality of internal and/or external mechanical and electromechanical components thereon and therein. In this disclosure, as is traditional, the term "proximal" will refer for example to the end of coagulator 10 (or other element) which is closer to the user, while the term "distal" will refer to the end which is further from the user.

Distal end 14 of housing 11 includes a distal port 17 which is designed to emit, expel or disperse gas emanating from an elongated gas supply channel or tube 60 that in this embodiment runs generally longitudinally through frame or housing 11 of coagulator 10. Tube 60 is for supplying pressurized gas 50 to an active electrode 350 located adjacent distal end 14 of housing 11. Preferably electrode 350 is proximal of port 17 and the gas that is emitted from port 17 is ionized. Elongated housing 11 includes a receptacle 25, preferably adjacent its proximal end 12, which receptacle can be or be part of a unitary or integral handle portion 12a of housing 11. Receptacle 25 is dimensioned to securely engage and receive or seat a gas pressurized container, canister, cartridge or cylinder 100 therein. Cylinder 100 contains a surgical gas, preferably a noble or inert gas, or mixture of noble or inert gases. References herein to inert gas or gases is understood to include noble gas or gases. The preferred inert gas is argon. Cylinder 100 preferably is relatively small, single use and disposable. Details of gas cylinder 100 and its selective engagement with or connection to housing 11 are discussed in more detail below with respect to FIGS. 2A-2C.

Elongated gas supply tube 60 is adapted and dimensioned to channel or carry pressurized gas 50 from cylinder 100 through a regulator or valve 30 to or through distal end 14 of coagulator 10 for ionization, preferably prior to the gas emitting and dispersing from distal port 17. Regulator or valve 30 can be part of or attached to cylinder 100, housing 11, or actuator 31. It is envisioned that distal port 17 or distal end 14 may be configured to facilitate or promote the dispersion of the ionized gas plasma 50' from distal port 17 in a uniform and consistent manner. For example, distal end 14 may be tapered on one, both or all sides thereof to direct the ionized plasma 50' toward surgical or operative site 410. Alternatively, distal port 17 may be configured to disrupt or aggravate the dispersion or flow of gas plasma 50' exiting distal port 17 to enhance coagulation by creating a more turbulent gas flow. It is contemplated that many suitable devices, e.g., screws, fans, blades, helical patterns, etc., may be employed to cause gas plasma 50' to flow more or less turbulently or with other predetermined flow characteristics through tube 60 and/or out of distal port 17.

Elongated housing 11, preferably its proximal end 12, is connected, for example, by an electrical cable 310, to a source of electrosurgical energy generally designated ESU, e.g., an electrosurgical generator 300. As mentioned above, proximal end 12 includes a receptacle 25 which receives, securely engages and seats cylinder 100 therein. Receptacle 25 and/or cylinder 100 need not be, as in the case of a single use disposable instrument, but preferably is or are configured to allow cylinder 100 to be selectively removable and replaceable within receptacle 25. For example and as best shown in FIG. 1, proximal end 12 of elongated housing 11, or receptacle 25 may include a locking mechanism 40 which upon insertion of a cylinder 100 into receptacle 25 preferably automatically (or manually) releasably locks the cylinder 100 securely within receptacle 25. By unlocking locking mechanism 40, cylinder 100 may be removed and replaced with another cylinder 100. It is envisioned that the locking mechanism 40 may be any suitable device or arrangement, for example a collar or clamp and may be spring loaded. For example, it may include two or more opposing spring clamps 42a, 42b which mechanically engage a corresponding one or more notches or cut outs 120a, 120b formed in the outer surface of gas cylinder 100. As can be appreciated, upon insertion of cylinder 100 into receptacle 35, the spring clamps 42a, 42b are positioned to allow entry of cylinder 100 into receptacle 25 until the spring clamps biasingly engage the notches 120a, 120b. It is envisioned that a locking mechanism 40 with spring clamps can be configured and adapted for releasably locking and quickly releasing the locking of cylinder 100 in receptacle 25. Preferably, the relative positioning and mechanical engagement of spring clamps 42a, 42b in notches 120a, 120b fully seats cylinder 100 within the receptacle such that a distal end 110 of cylinder 100 fully engages valve 30. The full seating of cylinder 100 in receptacle 25 can effect piecing or puncturing of the sealed distal end 110 of gas cylinder 100. Upon opening or actuation of valve 30, gas 50 is dispersed to elongated supply tube 60 as explained below.

Figure 1A:
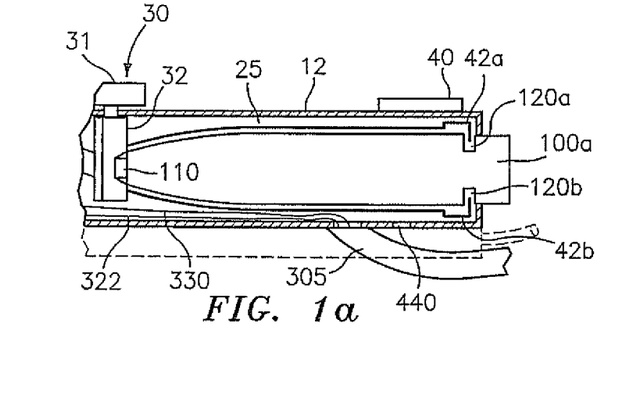
FIG. 1A is an enlarged view of the encircled portion of FIG. 1.
Figure 2A:
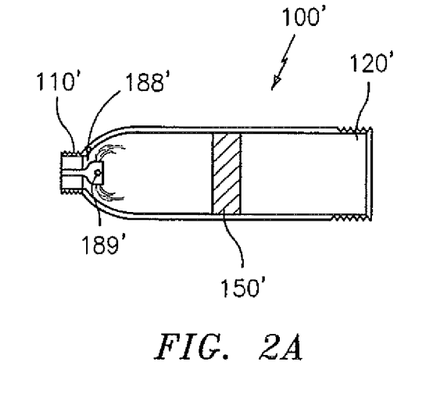
FIG. 2A is an enlarged schematic sectional view of an alternate embodiment of a gas cartridge for use with the electrosurgical coagulator of FIG. 1 having a color coded identification band and a safety valve.

A variety of other locking mechanisms may be utilized to secure gas cylinder 100 to or within receptacle 25. For example, the distal end 110 of cylinder 100 of FIG. 1a may be configured, e.g., threaded (as shown as 110' in FIG. 2A) to threadedly engage valve 30. Alternatively, as also shown in FIG. 2A, the proximal end of cylinder 100' may includes threads 120' which threadably engage the interior of receptacle 25 (not shown). Alternatively, proximal end 12 of housing 11 may be adapted to have an externally threaded collar or sleeve that extends axially outwardly and to have an internally threaded screw closure cap. With a cylinder seated in receptacle 25, the screw closing of the cap would push cylinder 100 distally against the bias of a spring onto an axially disposed piercing member to thereby break the seal at the distal tip of the cylinder. Removal of the closure cap would permit removal and replacement of the cylinder. The cap can be adapted to burst in the event of an internal overpressure, and additionally to include a pressure regulator or valve to control flow through the burst opening. Other locking mechanisms are also envisioned, for example snap locks, spring locks on the cylinder 100, locking levers, bayonet style locks, and locking dials or tabs, etc.

Electrosurgical instrument 10 includes at least one actuator, e.g., a dial or button, generally designated 31, for actuating and preferably selectively adjusting the flow of pressurized inert gas 50 from cylinder 100 to active electrode 350, and for actuating and preferably selectively adjusting the delivery of electrosurgical energy from the source, i.e., from generator 300, to the active electrode 350 for ionizing the inert gas for use at the surgical site 410. Actuator 31 for actuating the flow of pressurized gas from cylinder 100 can also operate as the actuator for actuating delivery of electrosurgical energy from the source. Actuator 31 may be referred to herein as the first actuator. It is envisioned that instead of being located in housing 11, actuator 31 can be located in a foot switch appropriately connected to coagulator 10.

Electrosurgical instrument or coagulator 10 can also include a second actuator, here shown as a button-like trigger 20, for actuating the delivery of electrosurgical energy from the source, e.g., from generator 300, through cable 310 and leads 322, 330 to the active electrode 350 for ionizing the inert gas for use at the surgical site 410. Trigger 20 can be attached to or mounted, for example, on or atop or through elongated housing 11. Trigger 20 may be any type of known trigger, e.g., a rocker switch, a handswitch, a footswitch, a slide switch, a dial, a button, a lever, etc., which, upon actuation thereof, electrically communicates with electrosurgical generator 300 to allow the selective delivery of electrosurgical energy to active electrode 350.

Active electrode 350 can be attached to or mechanically engaged with the distal end of the housing and positioned adjacent to or at an operating site 410. Preferably, active electrode 350 is positioned adjacent the distal end of frame or housing 11, preferably between the distal end of tube 60 and distal port 17, although the active electrode can be located just to the exterior of port 17. For example, active electrode 350 can be mounted to an elongated member that is supported within housing 11 and that extends outside of the housing, such that the electrode is positioned just outside of the port. Active electrode 350 need not be as shown. It can be a conductive elongated member in the form of a blade, needle, snare or ball electrode that extends from an electrosurgical instrument and that is suitable, for example, for fulguration, i.e., coagulation, cutting or sealing tissue.

As shown and in most monopolar electrosurgical systems, a return electrode or pad 370 is typically positioned under the patient and connected to a different electrical potential on electrosurgical generator 300 via cable 360. During activation, return pad 370 acts as an electrical return for the electrosurgical energy emanating from electrosurgical coagulator 10. It is envisioned that various types of electrosurgical generators 300 may be employed for this purpose, such as those generators sold by Valleylab, Inc. —a division of Tyco Healthcare Group LP, of Boulder, Colo.

It is envisioned that trigger 20, upon actuation thereof, is designed to energize electrode 350 in a simple "on/off" manner, e.g., when the trigger is depressed (or otherwise moved or manipulated, e.g., twisted (dial switch), rocked (rocker switch), or slid (slide switch)). Alternatively, it is contemplated that the electrical intensity from generator 300 may be selectively regulated by trigger 20, such that the user can alter the electrosurgical effect at operative site 410. For example a pressure sensitive trigger or regulator may be utilized to control the amount of electrosurgical energy that is conducted to electrode 350 which, as described below with respect to the operation of coagulator 10, effects coagulation of tissue 400. Triggers and actuators that are contemplated include those such as described in commonly-owned U.S. Provisional Application Ser. No. 60/424,352 and commonly-owned U.S. application Ser. No. 10/251,606, the entire contents of each of which are incorporated by reference herein, without intention of being limited to the same.

U.S. Provisional Application Ser. No. 60/424,352 discloses various flexible snap-dome switching devices for use in hand-held electrosurgical instruments for medical applications. The switching devices enable a surgeon to vary modes of operation of the instrument during surgery, e.g., for cutting or coagulation of tissue, and provide sensory feedback to the surgeon during use. In one disclosed embodiment, a switching device includes a substrate, an inner terminal disposed on an upper surface of the substrate and having a first height, an outer terminal, preferably ring-like, disposed on the upper surface of the substrate and substantially surrounding the inner terminal and having a second height which is greater than the height of the inner terminal, and a snap-dome secured to the substrate and having a periphery in electrical communication with the outer terminal. The snap-dome is depressible through a range wherein, upon inversion of the snap-dome, an apex of the snap dome electrically connects the inner and outer terminals. A tactile switch assembly can include an electrosurgical regulator which regulates the amount of electrosurgical energy transmitted upon activation of the tactile switch. The tactile switch assembly can include a second inner terminal wherein the first inner terminal has a first height. The second inner terminal, internal of the first inner terminal, has a second height which is less than the height of the first inner terminal. The outer terminal substantially surrounds the first inner terminal and defines a third height which is greater than the first height of the first inner terminal. The tactile switch assembly further includes a snap-dome secured to the substrate and having a periphery in electrical communication with the outer terminal. The snap-dome is depressible through a range wherein, upon depression of the snap-dome, an apex of the snap-dome electrically interconnects the first inner terminal and the outer terminal. Upon continued depression the apex electrically interconnects the second inner terminal and the outer terminal.

U.S. application Ser. No. 10/251,606, now publication No. 04-0092927 discloses an electrosurgical instrument having variable controls, a housing, and an electrocautery blade, an electrode, extending from the housing and connected to a source of electrosurgical energy. An actuator button supported on the housing is movable, e.g., depressed, or rocked or slid, from a first position to at least a subsequent position, preferably to a series of discrete subsequent positions wherein each subsequent position corresponds to a specific amount of energy being transmitted to the blade. Preferably, a transducer, e.g., a pressure transducer, or other suitable circuit element, is electrically connected between the activation button and the source of electrosurgical energy. The transducer is configured to transmit an electrical output signal, preferably a range of output signals, to the energy source correlating to the selected movement or position(s) of the activation button. The source correspondingly supplies an amount or range of electrosurgical energy emission to the blade dependent upon the electrical output signal(s). The above actuator and selectively adjustable system can be employed using at least one actuator, actuator 31, for actuating and preferably selectively adjusting the flow of pressurized gas from cylinder 100, e.g., via valve 30, and for actuating and preferably selectively adjusting delivery of energy from the source. Such can be achieved by employing, for example, a suitable transistor that produces a signal or two signals or different sets of output signals based on movement of the actuator button, the signal or one signal or set of signals being sent to and being suitable for actuating actuator 31 or valve 30 to actuate movement-correlated corresponding selectively adjusted flow of gas from the cylinder, and the signal or the other signal or set being sent to and being suitable for actuating trigger 20 to actuate movement-correlated corresponding selectively adjusted delivery of energy from the source. A similar suitable actuator system can be employed with one transistor to actuate a first actuator, actuator 31, for actuating and preferably selectively adjusting the flow from cylinder 100, and a second transistor to actuate a second actuator, trigger 20, for actuating and preferably selectively adjusting delivery of energy from the source. It is envisioned that instead of being located in housing 11, trigger 20 can be located in a foot switch appropriately connected to electrosurgical generator 300 and coagulator 10.

It is contemplated that the at least one actuator, e.g., actuator 31, is adapted or operated to actuate the release of pressurized gas 50 prior to actuating the delivery of electrosurgical energy from generator 300. When there is a first actuator and a second actuator, it is contemplated that the instrument or coagulator include one or more elements, e.g., circuitry, or mechanical or electromechanical mechanism(s), for timing the flow of gas from cylinder 100 and the delivery of energy to the electrode. Preferably, the first actuator is activated prior to the activation of the second actuator.

It is also contemplated that trigger 20 (or generator 300) may cooperate with one or more sensors 365 which can be attached to instrument 10, housing 11 or electrode 350 and which, for example, continually measures or monitors a condition e.g., at operative site 410, e.g., the amount of tissue coagulation, and relays the information back to generator 300 or trigger 20. For example, a control system or a safety circuit (not shown) may be employed which automatically, e.g., through a shut-off switch, cuts off the energy to tissue 400 and/or activates or releases a pressure relief valve or a safety release valve generally designated 367 for releasing the pressure of the pressurized gas based upon a sensed condition, e.g., embolic concern, by a sensor 365. It is also envisioned that based upon the sensed condition, gas cylinder 100 e.g., by valve 30, can be partially modulated, inactivated, rejected (or released) from engagement with valve coupling 32, or valve 30 may be automatically fully de-activated or closed. Alternatively, a sensor 365 may provide feedback to trigger 20 or generator 300 to optimize coagulation of the tissue 400 based upon tissue type or tissue response. A second sensor 321 may be employed to measure the flow of gas 50 through gas supply tube 60, and may be electrically connected to a flow regulator, e.g., valve 30, to automatically regulate the flow of gas from cylinder 100 to electrode 350.

As best shown in FIG. 1, the at least one actuator 31 preferably includes valve 30 which is mounted to and through elongated housing 11 and which can be dimensioned to mechanically engage and preferably also puncture or otherwise engage and open the sealed outlet at distal end 110 of selectively removable gas cylinder 100. Gas cylinder 100 can be removable in a reusable or disposable version of the instrument. Preferably, the mechanical engagement and securement of gas cylinder 100 and valve 30 involves a quick release type mechanism or other simple attachment mechanism which can be employed on and/or or as part of cylinder 100, receptacle 25 and/or housing 11 to enable the user to quickly and accurately engage and disengage and remove and replace gas cylinder 100. For example, various springs, levers, latches, slides and frictional engagement members, (not shown) may be employed to facilitate loading and quick removal of cylinder 100. As mentioned above, locking mechanism 40 may be employed to permanently or releasably secure cylinder 100 within receptacle 25.

Actuation of actuator 31 preferably activates valve 30. Valve 30 is for selectively or otherwise controlling or regulating the flow of gas from cylinder 100, and in an embodiment, to electrode 350. Valve 30 preferably includes a cylinder interface or coupling 32 and a plenum 34. Actuator 31 or valve 30 selectively adjusts plenum 34 to regulate, preferably selectively, the amount or flow of gas 50 from gas cylinder 100, to supply tube 60 and to electrode 350. It is envisioned that actuator 31 may be incrementally adjustable (i.e., rotatable, slideable or pressure sensitive) to provide tactile feedback to the user relating to the flow of gas 50. As can be appreciated, plenum 34 is disposed between coupling 32 and the proximal end 62 of supply tube 60. As mentioned above, coupling 32 mechanically engages (e.g., threadably engages, snap fits, friction-fits, slide fits, spring mounts, bayonets, or otherwise) cylinder 100 and preferably also breaks, pierces or otherwise opens the sealed distal end or outlet of cylinder 100 upon insertion of the cylinder 100 into receptacle 25. Although it is preferred that actuator 31 include valve 30, valve 30 can include actuator 31. Valve 30 may be referred to herein as a first flow regulator for selectively regulating the flow of pressurized gas from cylinder 100. In an embodiment, coagulator 10 can include a second flow regulator, "FR2", for selectively regulating the flow of pressurized gas to electrode 350. In an embodiment, coagulator 10 can include a pressure regulator, e.g., "PR" for regulating the pressure of the pressurized gas, e.g., that flows to electrode 350. In an embodiment, valve 30 can comprise a pressure regulator that includes a pressure relief valve in communication with cylinder 100 for regulating and/or relieving the pressure of the pressurized gas in the cylinder. Coagulator 10 preferably includes a flow limiter, for example, valve 30 may be or comprise a flow limiter, for limiting the flow of pressurized gas to electrode 350 to below a selected level.

Preferably, distal end 110 of cylinder 100 is hermetically sealed when and after it is mounted to and mechanically engaged with coupling 32 to avoid undesirable gas leakage from the mechanical connection. As can be appreciated, various rubber seals, gaskets, flanges or the like (not shown) may be employed to accomplish this purpose.

It is envisioned and preferred that valve 30 be opened, e.g., manually, to a desired flow rate prior to activation of electrode 350 to ionize the plasma to coagulate tissue 400. The same button, actuator or lever that actuates the delivery of energy would also activate valve 30 and the flow of gas. For example, the movement of a lever would actuate valve 30 and the flow of gas prior to continued movement of the lever to actuate delivery of energy from the generator. It is also contemplated that actuator 31 or valve 30 may be automatically regulated to communicate with trigger 20 and be automatically controlled by activation of trigger 20. For example, the user may select a flow rate by actuating actuator 31 (which may include a visual indicator or the like to allow the user to readily determine flow rate) such that upon actuation of trigger 20, valve 30 initiates the flow of gas 50 through tube 60 to the an ignition point 355 proximate electrode 350. Electrode 350 can, in turn, be activated to ionize the gas 50 and force the ionized gas plasma 50' at the tissue or operating site 410. Alternatively, actuation of actuator 31 or valve 30 can automatically activate actuation of trigger 20 and flow of electrosurgical energy to electrode 350.

Preferably, after actuation of trigger 20 and initiation of gas flow to ignition point 335, the ignition of the electrode 350 is delayed either mechanically, electro-mechanically or utilizing delay circuitry or a delay algorithm to preferably enhance delivery of plasma 50' to operating site 410. As can be appreciated, the delay circuitry or algorithm may be incorporated in trigger 20, valve 30 or generator 300.

During use, ionizable gas 50 is supplied under pressure from gas cylinder 100 to a flow regulator or valve 30 and, upon selective actuation of actuator 31, it flows to ignition point 335 near electrode 350 where gas 50 is ionized into a gas plasma 50' before being distributed, dispersed or dispensed out of distal end 17 to operating site 410. During use, the user may selectively alter the gas flow rate and/or the intensity of the energy emanating from electrode 350 to meet a desired surgical effect.

Preferably, gas cylinder 100 is relatively small and contains an appropriate or sufficient amount gas 50 for a given surgery of short duration. Cylinder 100 preferably is for single use, and is disposable. It may be replaced as needed during the surgical procedure if it requires a longer or different gas application than provided by a single gas cylinder. As can be appreciated, different gas cylinders 100 may be utilized for different surgeries which have different gas requirements, e.g., in terms of types, amounts, pressures and/or flow rates. The gas pressure of cylinders 100 preferably is about 3000 psi or less. Gas cylinders 100 preferably have a volume of about 100 cc's or less. Cylinders 100 containing about 4 liters of gas and a flow time of about 2 minutes have been found suitable for a typical coagulation procedure. For such procedures, the flow rate provided by the cylinder can range from about 0.2 liters/min. to about 4 liters/min, and the nominal flow rate may be about 2 liters/min. It is envisioned that cartridge 100 may be preconfigured to deliver gas at a predefined flow rate, and coagulator 10 may be configured without a flow regulator or flow valve 30 in or on elongated housing 11. Instead, elongated housing 11 may simply include an "open" and "close" switch (not shown) which blocks or releases the flow of gas from the gas cylinder 100 depending upon the position of the switch. As a result thereof, when opened, coagulator 10 relies on the predetermined flow rate of the gas 50 exiting the gas cylinder 100 under pressure. The gas flow rate employed is dependent upon factors such as the instrument being used and/or the type of surgery or procedure to be performed. Different gas cartridges, e.g., cylinder 100', can be premarked or coded, e.g., visibly, with a color, e.g., a colored band 150' (see FIG. 2A) to indicate a specific gas, as-filled flow rate or suitability for a particular instrument, procedure or application. Thus, a user may pick the appropriate color which specifically relates to a desired specific gas, flow rate and intended surgical use. Since cylinders 100 are easily replaceable, during surgery the user may opt to replace a cylinder 100 with a different cylinder 100' with a different flow rate (different color band 150'). Cylinder 100 may include a knob, e.g., 100a at the proximal end of the cylinder to facilitate manipulation of the cylinder.

FIG. 2A shows an embodiment of a gas cylinder 100' which includes a safety release pressure stop valve 188' which is designed to automatically prevent flow of gas from, or close the outlet at distal end 110' of cylinder 100' when the cylinder is removed. More particularly, upon release of the cylinder 100' from coupling 32, a ball 189' which (in a ball check valve or some other movable obstruction) because of residual gas pressure, automatically moves distally to block the passage of gas 50 through distal end 110' of the cylinder 100'. Upon insertion or engagement of the cylinder 100' into coupling 32, a pin or other protruding element (not shown) forces ball 189' proximally to allow the release of gas 50 from cylinder 100'. As can be appreciated, many different types of release pressure stops may be employed to accomplish the same or similar purpose and the above-described release pressure stop valve 188' is only one example. It is contemplated that cylinder 100 or the like, e.g., 100''', can include a safety pressure release valve "SPRV" to vent the gas prior to or when an active cylinder 100 is removed from receptacle 25 and/or to safely control release of cylinder internal gas overpressure. It is also contemplated that coagulator 10, e.g., receptacle 25 can include a pressure relief valve in communication with cylinder 100 for relieving the pressure of the pressurized gas in the cylinder.

Figure 2B:
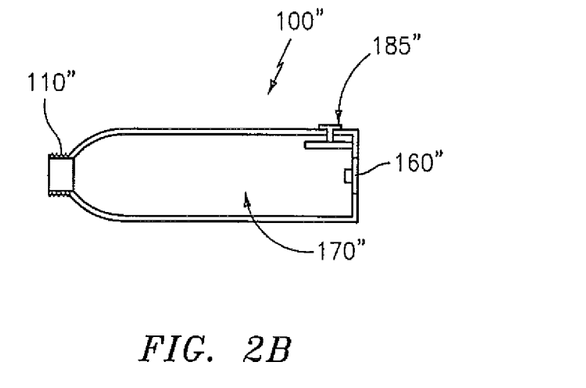
FIG. 2B is an enlarged schematic sectional view of a gas cartridge for use with the electrosurgical coagulator of FIG. 1 and having a volume gauge and a refilling port.

As best shown in FIG. 2B, an embodiment of gas cylinder 100", may include a gauge 185" which measures and indicates the amount of pressurized gas left in cylinder 100" at any given time. A visual or audible indicator or sensor (not shown) may be employed to alert the user of a low gas condition. Gas cylinder 100" may also include a fill port or refill valve 160" which enables the user to selectively refill interior 170" of gas cylinder 100" without removing the cylinder from within receptacle 25 of instrument 10.

Figure 2C:
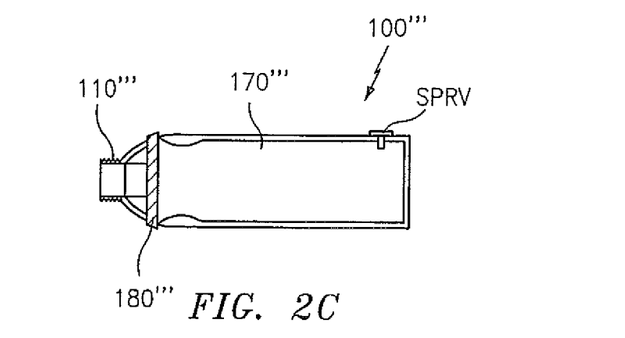
FIG. 2C is an enlarged schematic sectional view of a gas cartridge for use with the electrosurgical coagulator of FIG. 1 and having a flow regulator.

FIG. 2C shows another embodiment of gas cylinder 100''' which includes a valve 180''' disposed thereon which allows a user to selectively regulate gas flow from interior chamber 170''' through distal end 110''' and to coagulator 10. As such, a valve would not necessarily be needed within coagulator 10 and the user can selectively regulate gas 50 by rotating (or otherwise adjusting) valve 180''' as needed.

Figure 3A:
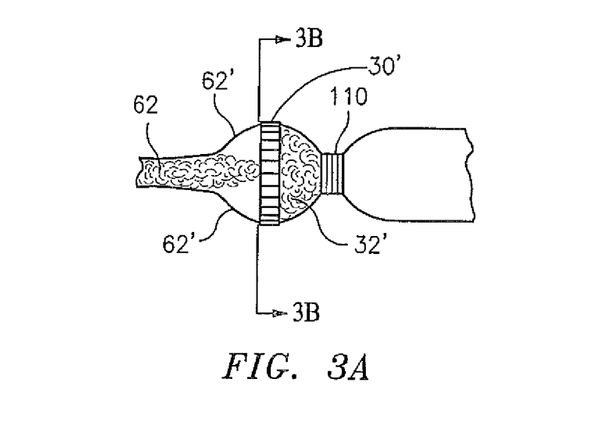
FIG. 3A is a greatly-enlarged schematic side plan view of an iris-like flow regulator for use with the electrosurgical coagulator of FIG. 1.
Figure 3B:
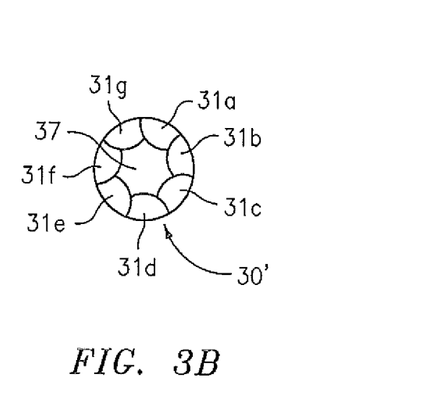
FIG. 3B is a cross sectional view of the iris-like flow regulator taken along line 3B-3B of FIG. 3A.

FIGS. 3A and 3B show an embodiment of a flow control valve, here shown as a rotary iris-like valve 30', which may be utilized within coagulator 10 (or with the gas cylinder 100''' as mentioned above) for selectively controlling the flow of pressurized gas from the cylinder. Iris valve 30' is preferably disposed between a coupling 32' and a flared portion 62' of proximal end 62 of supply tube 60. Upon rotation of iris valve 30' in a first direction, a series of interleaved portions 31a-31g move to radially reduce or condense the dimensions of passageway or opening 37 to limit gas flow therethrough and to the flared portion 62' of gas supply tube 60. Upon rotation of iris valve 30' in the opposite direction, the interleaved portions 31a-31g move to radially expand the dimensions of opening 37, enhancing gas flow therethrough and to the flared portion 62' of the supply tube 60.

It is envisioned that a corona return electrode or corona start electrode (not shown, but known in the art) may be utilized with electrode 350 to initiate a plasma arc. The corona return electrode may be placed on or within housing 11 located near distal end 14 or distal port 14. The corona return electrode is electrically connected to return path 360 of electrosurgical generator 300. The function of the corona return electrode is to establish a non-uniform electrical field with active electrode 350. The non-uniform electric field will cause the formation of a corona near active electrode 350, which will thereby aid in the ignition of gas 50 as it flows out of distal port 17 of the housing 11. Preferably, a dielectric member (not shown) is positioned to separate active electrode 350 from the corona return electrode.

From the foregoing and with reference to the various drawings, those skilled in the art will appreciate that not only can the electrosurgical instrument of the present disclosure, an embodiment of which is coagulator 10, be used to arrest bleeding tissue, but embodiments of the present disclosure can also be employed for desiccating surface tissue, eradicating cysts, forming eschars on tumors or thermically marking tissue. Those skilled in the art will also appreciate that certain modifications can also be made to the present disclosure without departing from the scope of the present disclosure.

For example, while several embodiments of the coagulator show an internally mounted cylinder 100 which fits within receptacle 25 of housing 11, it is envisioned that an externally mounted cylinder may be used to accomplish the same purpose. Moreover, although it is preferable to utilize argon as the ionizable gas for promulgating coagulation of the tissue, in some cases it may be preferably to use another ionizable gas or a combination of ionizable gases to effect the same or, a similar or different result.

Although the presently described coagulator employs a trigger which is designed to be hand-activated, including robotically, it is envisioned that a foot switch (not shown) may be utilized to activate the ionizing electrode. Moreover, it is also contemplated that the footswitch may be configured to house the gas cylinder therein. For example, the footswitch may include a receptacle for securely receiving a gas cylinder therein and a supply hose for transporting the flow of gas to and through the coagulator. As can be appreciated, this may be particularly advantageous since a larger gas cartridge may be provided in the foot switch than in the frame or handle of a hand held device, thus reducing the number of times that the user would have to replace the gas cartridge of the hand held device (if at all) during prolonged use. The gas supply hose may be attached to the electrosurgical cable which attaches to the proximal end of the coagulator to limit tangling.

It is also envisioned that the footswitch may not only contain the trigger for energizing the ionizing electrode but may also be configured to itself be or contain the actuator for releasing the flow of gas through the supply tube and to the surgical site.

Moreover, although shown as a pencil-like electrosurgical instrument or coagulator in the drawings, it is envisioned that the coagulator may include a pistol grip-like handle which enables the user to handle the instrument like a pistol. It is also contemplated that the cylinder may be dimensioned for selective engagement (i.e., insertion) within and disengagement (i.e., release) from the handle. Alternatively, the handle may be selectively pivotable for handling the coagulator in different orientations, e.g., from an offset position relative to the housing for handling the coagulator in pistol-like fashion to a generally aligned orientation for handling the coagulator like a pencil.

It is envisioned that the electrosurgical instrument or coagulator and the cylinders may be completely disposable or the coagulator may be reposable and the cylinders disposable. Moreover, the mechanically engaging distal end of the cylinders may be designed for easy retrofits onto exiting coagulators. It is envisioned that instrument 10, for example, housing 11 or actuator 31 can include a second flow regulator (not shown) to regulate the flow of gas to active electrode 350.

There have been described and illustrated herein several embodiments of a coagulator for arresting bleeding and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

It is envisioned that instrument 10, for example, housing 11 or actuator 30 can include a second flow regulator, "FR2", to regulate the flow of gas to active electrode 350.

What is claimed is:

1. An electrosurgical instrument for providing ionized gas to a surgical site, comprising:
    an elongated housing having a proximal end and a distal end, the elongated housing being configured for operable connection with a source of pressurized gas;
    an active electrode mounted at least partially within the elongated housing adjacent the distal end of the elongated housing, the electrode adapted to connect to a source of electrosurgical energy;
    at least one actuator which actuates the flow of pressurized inert gas from the source of pressurized gas over a portion of the active electrode within the elongated housing and which actuates the delivery of electrosurgical energy from the source of electrosurgical energy to the active electrode for ionizing the pressurized inert gas flowing over the active electrode for use at the surgical site;
    a flow regulator at least partially disposed within the elongated housing for selectively regulating the flow of pressurized gas from the source of pressurized gas upon actuation of the at least one actuator; and
    a sensor at least partially disposed on the elongated housing and in electrical communication with the flow regulator, the sensor being configured to sense a selected condition at the surgical site and automatically control the regulation of flow of pressurized gas to the active electrode.

2. The electrosurgical instrument according to claim 1, wherein the at least one actuator is adapted to actuate the release of pressurized gas from the source of pressurized gas prior to actuating the delivery of the electrosurgical energy from the source.

3. The electrosurgical instrument according to claim 1, wherein the at least one actuator includes a first actuator which actuates the flow of pressurized gas from the source of pressurized gas and a second actuator which actuates delivery of the electrosurgical energy from the source of electrosurgical energy to the active electrode.

4. The electrosurgical instrument according to claim 3, wherein the first actuator is actuated prior to actuating the second actuator.

5. The electrosurgical instrument according to claim 4, wherein the second actuator which actuates the delivery of electrosurgical energy from the electrosurgical energy source is adapted to selectively adjust the amount of electrosurgical energy that is delivered to the active electrode.

6. The electrosurgical instrument according to claim 4, wherein the first actuator which actuates the flow of pressurized gas from the cylinder is adapted to selectively adjust the flow of pressurized gas from the cylinder.

7. The electrosurgical instrument according to claim 3, wherein the sensor is in electrical communication with the second actuator which actuates delivery of electrosurgical energy from the source, the sensor being configured to sense a selected condition and automatically modulate the delivery of energy to the active electrode.

8. The electrosurgical instrument according to claim 1, wherein the source of pressurized gas includes a cylinder having a sealed outlet and the elongated housing includes a coupling which is configured to rupture the sealed outlet upon reception of the cylinder with the elongated housing.

9. The electrosurgical instrument according to claim 1, further comprising:
a pressure regulator which regulates the pressure of the pressurized gas flowing over the active electrode.

10. The electrosurgical instrument according to claim 1, further comprising:
a selectively releasable locking mechanism configured to releasably engage the source or pressurized gas.

11. The electrosurgical instrument according to claim 1, further comprising:
a second flow regulator which selectively regulates the flow of pressurized gas over the active electrode.

12. The electrosurgical instrument according to claim 1, further comprising:
a pressure relief valve for relieving the pressure of the pressurized gas.

13. The electrosurgical instrument according to claim 12, wherein the sensor is in electrical communication with the pressure relief valve to sense a selected condition and automatically activates the pressure relief valve to relieve the pressure of the pressurized inert gas in the cylinder.

14. The electrosurgical instrument according to claim 1, further comprising:
a flow limiter which limits the flow of pressurized gas over the active electrode.

15. The electrosurgical instrument according to claim 1, wherein the instrument is configured and adapted for use in closed procedures.

16. The electrosurgical instrument of claim 1, wherein the elongated housing is configured for pencil-grip engagement by a user.

17. An electrosurgical instrument for providing ionized gas to a surgical site, comprising:
an elongated housing having a proximal end and a distal end, the elongated housing being configured for operable connection with a source of pressurized gas;
an active electrode mounted within the distal end of the elongated housing, the electrode adapted to connect to a source of electrosurgical energy;
at least one actuator operably supported on the elongated housing which is selectively adjustable to control the flow of pressurized gas from the source of pressurized gas over at least a portion of the active electrode within the elongated housing and the delivery of electrosurgical energy from the source of electrosurgical energy to the active electrode for ionizing the pressurized inert gas for use at the surgical site; and
a sensor at least partially disposed on the elongated housing, the sensor being configured to sense a selected condition at the surgical site and automatically control the regulation of flow of pressurized gas to the active electrode.

18. An electrosurgical instrument for providing ionized gas to a surgical site, comprising:
an elongated housing having a proximal end and a distal end, the elongated housing being configured for operable connection with a source of pressurized gas;
an active electrode mounted entirely within the elongated housing adjacent the distal end of the elongated housing, the electrode adapted to connect to a source of electrosurgical energy;
a flow regulator at least partially disposed within the elongated housing for regulating the flow of pressurized gas from the source of pressurized gas over the active electrode; and
a sensor at least partially disposed on the elongated housing and in electrical communication with the flow regulator, the sensor being configured to sense a selected condition at the surgical site and automatically control the regulation of flow of pressurized gas to the active electrode.

19. An electrosurgical instrument for providing ionized gas to a surgical site, comprising:
an elongated housing having a proximal end and a distal end, the elongated housing being configured to selectively receive a cylinder of pressurized gas;
an active electrode mounted within the distal end of the elongated housing, the electrode adapted to connect to a source of electrosurgical energy;
at least one actuator which actuates the flow of pressurized gas from the cylinder over a portion of the active electrode within the elongated housing and which actuates the delivery of electrosurgical energy from the source of electrosurgical energy to the active electrode for ionizing the pressurized inert gas for use at the surgical site; and
a sensor at least partially disposed on the elongated housing for sensing a condition at the surgical site, the sensor being electrically connected to a safety pressure relief valve which vents pressure from the source of pressurized gas before the source of pressurized gas is removed from the elongated housing.

20. An electrosurgical system for performing an electrosurgical procedure on a patient, the system comprising:
a source of electrosurgical energy;
a source of pressurized gas; and
an electrosurgical instrument including:
an elongated housing having a proximal end and a distal end, the elongated housing being configured for operable connection with a source of pressurized gas;
an active electrode mounted completely within the distal end of the elongated housing, the electrode adapted to connect to the source of electrosurgical energy;
at least one actuator operably supported on the elongated housing which is selectively adjustable to control the flow of pressurized gas from the source of pressurized gas over at least a portion of the active electrode and the delivery of electrosurgical energy from the source of electrosurgical energy to the active electrode for ionizing the pressurized inert gas for use at the surgical site; and
a sensor at least partially disposed on the elongated housing, the sensor being configured to sense a selected condition at a surgical site and automatically control the regulation of flow of pressurized gas to the active electrode.

* * * * *